(12) United States Patent
Head et al.

(10) Patent No.: US 6,322,968 B1
(45) Date of Patent: *Nov. 27, 2001

(54) *DE NOVO* OR "UNIVERSAL" SEQUENCING ARRAY

(75) Inventors: Steven R. Head, Manchester; Philip Goelet, Reistertown, both of MD (US); Jonathan Karn, Cambridge (GB); Michael Boyce-Jacino, Finksburg, MD (US)

(73) Assignee: Orchid BioSciences, Inc., Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/976,427

(22) Filed: Nov. 21, 1997

(51) Int. Cl.[7] ............................................. C12Q 1/68
(52) U.S. Cl. ........................... 435/6; 536/24.3; 435/287.2
(58) Field of Search ........................ 536/24.3; 435/287.2, 435/6

(56) References Cited

U.S. PATENT DOCUMENTS

| | | | |
|---|---|---|---|
| 4,656,127 | 4/1987 | Mundy | 435/6 |
| 4,812,856 | 3/1989 | Wallace | 346/1.1 |
| 5,151,507 | 9/1992 | Hobbs, Jr. et al. | |
| 5,302,509 | 4/1994 | Cheeseman | 435/6 |
| 5,445,933 | * 8/1995 | Eadie et al. | 435/6 |
| 5,445,934 | 8/1995 | Fodor et al. | 435/6 |
| 5,547,839 | 8/1996 | Dower et al. | 435/6 |
| 5,599,695 | 2/1997 | Pease et al. | |
| 5,691,141 | 11/1997 | Köster | |

FOREIGN PATENT DOCUMENTS

| | | |
|---|---|---|
| 2650840 | 2/1991 | (FR). |
| WO 89/10414 | 11/1989 | (WO). |
| WO 92/15712 | 9/1992 | (WO). |
| WO 95/00669 | 1/1995 | (WO). |
| WO 95/11995 | 5/1995 | (WO). |

OTHER PUBLICATIONS

Guo et al., Direct fluorescence analysis of genetic polymorphisms by hybridization with oligonucleotide arrays on glass supports, *Nucleic Acids Research*, vol. 22, No. 24 pp. 5456–5465 (1994).

Chetverin, A.B., et al., "Oligonucleotide Arrays: New Concepts And Possibilities," BioTechnology, 12:1093–1099 (1994).

Kornher, J. S. et al., "Mutation Detection Using Nucleotide Analogs That Alter Electrophoretic Mobility," Nucleic Acids Research, 17:7779–7784 (1989).

Sokolov, B.P., "Primer Extension Technique For The Detection Of Single Nucleotide In Genomic DNA," Nucleic Acids Research 18:3671 (1990).

(List continued on next page.)

*Primary Examiner*—Scott W. Houtteman
(74) *Attorney, Agent, or Firm*—Kalow & Springut LLP

(57) ABSTRACT

The present invention describes a novel nucleic acid sequencing reagent which consists of a capture moiety, a spacer region and a sequence specific hybridizing region of 4–8 bases. The nucleic acid sequencing reagent of the present invention can also contain an attachment moiety. The nucleic acid sequencing reagent can be arranged into a nested array. This array configuration can then be used to sequence a given template without prior knowledge (de novo) of the wild type or expected sequence in conjunction with primer extension in the presence of a labeled chain terminating nucleotide.

22 Claims, 2 Drawing Sheets

OTHER PUBLICATIONS

Syvänen, A–C, et al., "A Primer–Guided Nucleotide Incorporation Assay in the Genotyping of Apolipoprotein E," Genomics 8:684–692 (1990).

Kuppuswamy, M.N., "Single Nucleotide Primer Extension To Detect Genetic Diseases: Experimental Application To Hemophilia B (Factor IX) And Cystic Fibrosis Genes," Proc. Natl. Acad. Sci. USA 88: 1143–1147 (1991).

Ugozzoli, L., "Detection Of Specific Alleles By Using Allele–Specific Primer Extension Followed By Capture On Solid Support," GATA 9(4): 107–112 (1992).

Nyrén, P., et al., "Solid phase DNA Minisequencing by an Enzymatic Luminometric Inorganic Pyrophosphate Detection Assay," Analytical Biochemistry 208:171–175 (1993).

Pastinen, T., et al., "Minisequencing: A specific tool for DNA analysis and diagnostics on oligonucleotide arrays," Genome Research 7:606–614 (1997).

Pastinen, T., et al., "Multiplex, Fluorescent, Solid–Phase Minisequencing For Efficient Screening Of DNA Sequence Variation," Clinical Chemistry 42:3191–3197 (1996).

Shumaker, J.M., et al., "Mutation Detection by Solid Phase Primer Extension," Human Mutation 7:346–354 (1996).

Prezant, T.R., et al., "Trapped–Oligonucleotide Nucleotide Incorporation (TONI) Assay, a Simple Method for Screening Points Mutations," Human Mutation 1:159–164 (1992).

* cited by examiner

SEQUENCE LISTING

<160> NUMBER OF SEQ ID NOS: 31

<210> SEQ ID NO 1
<211> LENGTH: 45
<212> TYPE: DNA
<213> ORGANISM: Artificial Sequence
<220> FEATURE:
<223> OTHER INFORMATION: Synthetic primer

<400> SEQUENCE: 1
gggggggggg gggggggggg ctagtggaaa tagtttcatg ttcat       5

<210> SEQ ID NO 2
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 2
cccccccccc ccccccccnn nnnnnntttc c       31

<210> SEQ ID NO 3
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 3
cccccccccc ccccccccnn nnnnnnttcc a       31

<210> SEQ ID NO 4
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 4
cccccccccc ccccccccnn nnnnntcca c       31

<210> SEQ ID NO 5
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 5
cccccccccc ccccccccnn nnnnnattt c       31

<210> SEQ ID NO 6
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 6
cccccccccc ccccccccnn nnnnntatt t       31

<210> SEQ ID NO 7
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 7
cccccccccc ccccccccnn nnnnnctat t                                    31

<210> SEQ ID NO 8
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 8
cccccccccc ccccccccnn nnnnnacta t                                    31

<210> SEQ ID NO 9
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 9
cccccccccc ccccccccnn nnnnnaact a                                    31

<210> SEQ ID NO 10
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 10
cccccccccc ccccccccnn nnnnnaaac t                                    31

<210> SEQ ID NO 11
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 11
cccccccccc ccccccccnn nnnnngaaa c                                    31

<210> SEQ ID NO 12
<211> LENGTH: 30
<212> TYPE: DNA

<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 12
cccccccccc ccccccccnn nnnnnnttcc                                    30

<210> SEQ ID NO 13
<211> LENGTH: 30
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 13
cccccccccc ccccccccnn nnnnnntcca                                    30

<210> SEQ ID NO 14
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 14
cccccccccc ccccccccnn nnnnnntcca c                                  31

<210> SEQ ID NO 15
<211> LENGTH: 30
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 15
cccccccccc ccccccccnn nnnnnnccac                                    30

<210> SEQ ID NO 16
<211> LENGTH: 51
<212> TYPE: DNA
<213> ORGANISM: Artificial Sequence
<220> FEATURE:
<223> OTHER INFORMATION: Synthetic primer

<400> SEQUENCE: 16
gggggggggg gggggggggg tgtggcctag tggaaatagt taacgcgact g            51

<210> SEQ ID NO 17
<211> LENGTH: 30
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

-continued

<400> SEQUENCE: 17
cccccccccc ccccccccnn nnnnncgcg                                                30

<210> SEQ ID NO 18
<211> LENGTH: 32
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(25)

<400> SEQUENCE: 18
cccccccccc ccccccccnn nnnncccg cg                                              32

<210> SEQ ID NO 19
<211> LENGTH: 30
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 19
cccccccccc ccccccccnn nnnnnggcc                                                30

<210> SEQ ID NO 20
<211> LENGTH: 32
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(25)

<400> SEQUENCE: 20
cccccccccc ccccccccnn nnnncccgg cc                                             32

<210> SEQ ID NO 21
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 21
cccccccccc ccccccccnn nnnnnaggc c                                              31

<210> SEQ ID NO 22
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 22
cccccccccc ccccccccnn nnnnncggc c                                              31

<210> SEQ ID NO 23
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 23 ccccccccc cccccccnn nnnnngggc c                               31

<210> SEQ ID NO 24
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 24 ccccccccc cccccccnn nnnnntggc c                               31

<210> SEQ ID NO 25
<211> LENGTH: 17
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (1)...(12)

<400> SEQUENCE: 25
nnnnnnnnnn nnactat                                            17

<210> SEQ ID NO 26
<211> LENGTH: 25
<212> TYPE: DNA
<213> ORGANISM: Artificial Sequence
<220> FEATURE:
<223> OTHER INFORMATION: Synthetic primer

<400> SEQUENCE: 26 ccccccccc ccccccccc ccccc                                     25

<210> SEQ ID NO 27
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 27
tgtgtgtgtg tgtgtgtgnn nnnnnacta t                             31

<210> SEQ ID NO 28
<211> LENGTH: 18
<212> TYPE: DNA
<213> ORGANISM: Artificial Sequence
<220> FEATURE:
<223> OTHER INFORMATION: Synthetic primer -continued

```
<400> SEQUENCE: 28
tgtgtgtgtg tgtgtgtg                                                         18

<210> SEQ ID NO 29
<211> LENGTH: 50
<212> TYPE: DNA
<213> ORGANISM: Artificial Sequence
<220> FEATURE:
<223> OTHER INFORMATION: Synthetic primer

<400> SEQUENCE: 29
ctagtggaaa tagtttcatg ttcagtgtgt gggggggggg gggggggggg                      50

<210> SEQ ID NO 30
<211> LENGTH: 30
<212> TYPE: DNA
<213> ORGANISM: Artificial Sequence
<220> FEATURE:
<223> OTHER INFORMATION: Synthetic primer

<400> SEQUENCE: 30
ctagtggaaa tagtttcatg ttcagtgtgt                                            30

<210> SEQ ID NO 31
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: unsure
<222> LOCATION: (19)...(26)

<400> SEQUENCE: 31 ccccccccc ccccccccnn nnnnnntatt tcc                                         33
```

DE NOVO OR "UNIVERSAL" SEQUENCING ARRAY

FIELD OF THE INVENTION

The present invention relates to a nucleic acid sequencing reagent based on a combinatorial array of 4–8 specific bases, combined with one or more random bases or other spacer molecules, and a "generic" template capture moiety capable of binding to some common region of the template nucleic acid. Template nucleic acids, such as DNA amplified by PCR, can be sequenced or scanned for mutations using this array configuration through primer extension with labeled ddNTPs. This array can also be used to sequence templates without prior knowledge (de novo) of the wild type or "expected" sequence.

BACKGROUND OF THE INVENTION

I. NUCLEIC ACID SEQUENCING

Initial attempts to determine the sequence of a DNA molecule were extensions of techniques which had been initially developed to permit the sequencing of RNA molecules (Sanger, F., *J. Mol. Biol.* 13:373 (1965); Brownlee, G. G. et al., *J. Mol. Biol.* 34:379 (1968)). Such methods involved the specific cleavage of DNA into smaller fragments by (1) enzymatic digestion (Robertson, H. D. et al., *Nature New Biol.* 241:38 (1973); Ziff, E. B. et al., *Nature New Biol.* 241:34 (1973)); (2) nearest neighbor analysis (Wu, R., et al., *J. Mol. Biol.* 57:491 (1971)), and (3) the "Wandering Spot" method (Sanger, F., *Proc. Natl. Acad. Sci. (U.S.A.)* 70:1209 (1973)).

The most commonly used methods of nucleic acid sequencing are the dideoxy-mediated chain termination method, also known as the "Sanger Method" (Sanger, F., et al., *J. Molec. Biol.* 94:441 (1975); Prober, J. et al., *Science* 238:336–340 (1987)) and the "chemical degradation method," also known as the "Maxam-Gilbert method" (Maxam, A. M., et al., *Proc. Natl. Acad. Sci. (U.S.A.)* 74:560 (1977), both references herein incorporated by reference).

A. The Maxam-Gilbert Method Of DNA Sequencing

The Maxam-Gilbert method of DNA sequencing is a degradative method. In this procedure, a fragment of DNA is labeled at one end (or terminus) and partially cleaved in four separate chemical reactions, each of which is specific for cleaving the DNA molecule at a particular base (G or C) at a particular type of base (A/G, C/T, or A>C). As in the dideoxy method, the effect of such reactions is to create a set of nested molecules whose lengths are determined by the locations of a particular base along the length of the DNA molecule being sequenced. The nested reaction products are then resolved by electrophoresis, and the end-labeled molecules are detected, typically by autoradiography when a $^{32}P$ label is employed. Four single lanes are typically required in order to determine the sequence.

Significantly, in the Maxam-Gilbert method the sequence is obtained from the original DNA molecule, and not from an enzymatic copy. For this reason, the method can be used to sequence synthetic oligonucleotides, and to analyze DNA modifications such as methylation, etc. It can also be used to study both DNA secondary structure and protein-DNA interactions. Indeed, it has been readily employed in the identification of the binding sites of DNA binding proteins.

The Maxam-Gilbert method uses simple chemical reagents which are readily available. Nevertheless, the dideoxy-mediated method has several advantages over the Maxam-Gilbert method. The Maxam-Gilbert method is extremely laborious and requires meticulous experimental technique. In contrast, the Sanger method may be employed on larger nucleic acid molecules.

B. Dideoxy-Mediated Chain Termination Method Of DNA Sequencing

In the dideoxy-mediated or "Sanger" chain termination method of DNA sequencing, the sequence of a DNA molecule is obtained through the extension of an oligonucleotide primer which is hybridized to the nucleic acid molecule being sequenced. In brief, four separate primer extension reactions are conducted. In each reaction, a DNA polymerase is added along with the four nucleotide triphosphates needed to polymerize DNA. Each of these reactions is carried out in the additional presence of a 2',3' dideoxy derivative of the A, T, C, or G nucleoside triphosphate. Such derivatives differ from conventional nucleoside triphosphates in that they lack a hydroxyl residue at the 3' position of deoxyribose. Thus, although they can be incorporated by a DNA polymerase into the newly synthesized primer extension, the absence of the 3' hydroxyl group causes them to be incapable of forming a phosphodiester bond with a succeeding nucleoside triphosphate. The incorporation of a dideoxy derivative results in the termination of the extension reaction.

Because the dideoxy derivatives are present in lower concentrations than their corresponding, conventional nucleoside triphosphate analogs, the net result of each of the four reactions is to produce a set of nested oligonucleotides each of which is terminated by the particular dideoxy derivative used in the reaction. By subjecting the reaction products of each of the extension reactions to electrophoresis, it is possible to obtain a series of four "ladders." Since the position of each "rung" of the ladder is determined by the size of the molecule, and since such size is determined by the incorporation of the dideoxy derivative, the appearance and location of a particular "rung" can be readily translated into the sequence of the extended primer. Thus, through an electrophoretic analysis, the sequence of the extended primer can be determined.

Methods for sequencing DNA using either the dideoxy-mediated method or the Maxam-Gilbert method are widely known to those of ordinary skill in the art. Such methods are, for example, disclosed in Maniatis, T. et al., *Molecular Cloning, a Laboratory Manual*, 2nd Edition, Cold Spring Harbor Press, Cold Spring Harbor, N. Y. (1989), and in Zyskind, J. W. et al., *Recombinant DNA Laboratory Manual*, Academic Press, Inc., New York (1988), both of which are herein incorporated by reference.

Both the dideoxy-mediated method and the Maxam-Gilbert method of DNA sequencing require the prior isolation of the DNA molecule which is to be sequenced. The sequence information is obtained by subjecting the reaction products to electrophoretic analysis (typically using polyacrylamide gels). Thus, a sample is applied to a lane of a gel, and the various species of nested fragments are separated from one another by their migration velocity through the gel.

C. Sequencing Via Hybridization To Ordered Oligonucleotide Arrays

In response to the difficulties encountered in employing gel electrophoresis to analyze sequences, alternative methods have been developed. Existing methods for de novo sequencing on solid phase arrays consist primarily of hybridization of template nucleic acids to arrayed primers containing combinatorial sequences which hybridize to complementary sequences on the template strand. These methods combine the capture of the template, by formation of stable duplex structures, with sequence discrimination due to instability of mismatches between the template and the primer. Chetverin, A. B. et al. provides a general review of solid-phase oligonucleotide synthesis and hybridization techniques. Chetverin, A. B. et al., *Bio/Technology* 12:1093–1099 (1994).

Macevicz (U.S. Pat. No. 5,002,867), for example, describes a method for determining nucleic acid sequence via hybridization with multiple mixtures of oligonucleotide probes. In accordance with this method, the sequence of a target polynucleotide is determined by permitting the target to sequentially hybridize with sets of probes having an invariant nucleotide at one position, and a variant nucleotides at other positions. The Macevicz method determines the nucleotide sequence of the target by hybridizing the target with a set of probes, and then determining the number of sites that at least one member of the set is capable of hybridizing to the target (i.e., the number of "matches"). This procedure is repeated until each member of a sets of probes has been tested.

Beattie, W. G. et al. has described a protocol for the preparation of terminal amine-derivatized 9-mer oligonucleotide arrays on ordinary microscope slides. Beattie, W. G. et al., *Molec. Biotech.* 4:213–225 (1995). These oligonucleotide arrays can hybridize DNA target strands of up to several hundred bases in length and can discriminate against mismatches.

Drmanac, R. T. has described a method for sequencing nucleic acid by hybridisation using nucleic acid segments on different sectors of a substrate and probes which discriminate between a one base mismatch. Drmanac, R. T. (EP 797683). Gruber, L. S. describes a method for screening a sample for the presence of an unknown sequence using hybridization sequencing. Gruber, L. S. (EP 787183).

D. Microsequencing and GBA™ Genetic Analysis

In contrast to the "Sanger Method" and the "Maxam-Gilbert method," which identify the sequence of all of the nucleotides of a target polynucleotide, "microsequencing" methods determine the identity of only a single nucleotide at a "predetermined" site. Such methods have particular utility in determining the presence and identity of polymorphisms in a target polynucleotide.

Because single nucleotide polymorphisms constitute sites of variation flanked by regions of invariant sequence, their analysis requires no more than the determination of the identity of the single nucleotide present at the site of variation; it is unnecessary to determine a complete gene sequence for each patient. Several methods have been developed to facilitate the analysis of such single nucleotide polymorphisms.

Several primer-guided nucleotide incorporation procedures for assaying polymorphic sites in DNA have been described (Komher, J. S. et al., *Nucl. Acids. Res.* 17:7779–7784 (1989); Sokolov, B. P., *Nucl. Acids Res.* 18:3671 (1990); Syvänen, A.-C., et al., *Genomics* 8:684–692 (1990); Kuppuswamy, M. N. et al., *Proc. Natl. Acad. Sci. (U.S.A.)* 88:1143–1147 (1991); Prezant, T. R. et al., *Hum. Mutat.* 1:159–164 (1992); Ugozzoli, L. et al., GATA 9:107–112 (1992); Nyrén, P. et al., *Anal. Biochem.* 208:171–175 (1993); and Wallace, WO89/10414). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvänen, A.-C. et al., *Amer. J. Hum. Genet.* 52:46–59 (1993)). Such a range of locus-specific signals could be more complex to interpret, especially for heterozygotes, compared to the simple, ternary (2:0, 1:1, or 0:2) class of signals produced by the GBA™ method. In addition, for some loci, incorporation of an incorrect deoxynucleotide can occur even in the presence of the correct dideoxynucleotide (Komher, J. S. et al., *Nucl. Acids. Res.* 17:7779–7784 (1989)). Such deoxynucleotide misincorporation events may be due to the Km of the DNA polymerase for the mispaired deoxy-substrate being comparable, in some sequence contexts, to the relatively poor Km of even a correctly base paired dideoxy-substrate (Kornberg, A. et al., In: *DNA Replication*, Second Edition (1992), W. H. Freeman and Company, New York; Tabor, S. et al., *Proc. Natl. Acad. Sci. (U.S.A.)* 86:4076–4080 (1989)). This effect would contribute to the background noise in the polymorphic site interrogation.

The GBA™ Genetic Bit Analysis method disclosed by Goelet, P. et al. (WO 92/15712, herein incorporated by reference) is a particularly useful microsequencing method. In GBA™, the nucleotide sequence information surrounding a predetermined site of interrogation is used to design an oligonucleotide primer that is complementary to the region immediately adjacent to, but not including, the predetermined site. The target DNA template is selected from the biological sample and hybridized to the interrogating primer. This primer is extended by a single labeled dideoxynucleotide using DNA polymerase in the presence of at least two, and most preferably all four chain terminating nucleoside triphosphate precursors.

Mundy, C. R. (U.S. Pat. No. 4,656,127) discusses alternative microsequencing methods for determining the identity of the nucleotide present at a particular polymorphic site. Mundy's method employs a specialized exonuclease-resistant nucleotide derivative. A primer complementary to the allelic sequence immediately 3'-to the polymorphic site is permitted to hybridize to a target molecule obtained from a particular animal or human. If the polymorphic site on the target molecule contains a nucleotide that is complementary to the particular exonucleotide-resistant nucleotide derivative present, then that derivative will be incorporated by a polymerase onto the end of the hybridized primer. Such incorporation renders the primer resistant to exonuclease, and thereby permits its detection. Since the identity of the exonucleotide-resistant derivative of the sample is known, a finding that the primer has become resistant to exonucleases reveals that the nucleotide present in the polymorphic site of the target molecule was complementary to that of the nucleotide derivative used in the reaction. Mundy's method has the advantage that it does not require the determination of large amounts of extraneous sequence data. It has the disadvantages of destroying the amplified target sequences, and unmodified primer and of being extremely sensitive to the rate of polymerase incorporation of the specific exonuclease-resistant nucleotide being used.

Cohen, D. et al. (French Patent 2,650,840; PCT Appln. No. WO91/02087) discuss a solution-based method for determining the identity of the nucleotide of a polymorphic site. As in the Mundy method of U.S. Pat. No. 4,656,127, a primer is employed that is complementary to allelic sequences immediately 3'-to a polymorphic site. The method determines the identity of the nucleotide of that site using labeled dideoxynucleotide derivatives, which, if complementary to the nucleotide of the polymorphic site will become incorporated onto the terminus of the primer.

In contrast to the method of Cohen et al. (French Patent 2,650,840; PCT Appln. No. WO91/02087), the GBA™ method of Goelet, P. et al. can be conducted as a heterogeneous phase assay, in which the primer or the target molecule is immobilized to a solid phase. It is thus easier to perform, and more accurate than the method discussed by Cohen. The method of Cohen has the significant disadvantage of being a solution-based extension method that uses labeled dideoxynucleoside triphosphates. In the Cohen method, the target DNA template is usually prepared by a DNA amplification reaction, such as the PCR, that uses a high concentration of deoxynucleoside triphosphates, the natural substrates of DNA polymerases. These monomers will compete in the subsequent extension reaction with the dideoxynucleoside triphosphates. Therefore, following the PCR reaction, an additional purification step is required to separate the DNA template from the unincorporated dNTPs. Because it is a solution-based method, the unincorporated dNTPs are difficult to remove and the method is not suited for high volume testing.

Cheesman, P. (U.S. Pat. No. 5,302,509) describes a method for sequencing a single stranded DNA molecule using fluorescently labeled 3'-blocked nucleotide triphosphates. An apparatus for the separation, concentration and detection of a DNA molecule in a liquid sample has been recently described by Ritterband, et al. (PCT Patent Application No. WO95/17676). Dower, W. J. et al. (U.S. Pat. No. 5,547,839) describes a method for sequencing an immobilized primer using fluorescent labels.

Chee, M. et al. (WO95/11995) describes an array of primers immobilized onto a solid surface. Chee et al. further describes a method for determining the presence of a mutation in a target sequence by comparing against a reference sequence with a known sequence.

An alternative approach, the "Oligonucleotide Ligation Assay" ("OLA") (Landegren, U. et al., *Science* 241:1077–1080 (1988)) has also been described as being capaole of detecting single nucleotide polymorphisms. The OLA protocol uses two oligonucleotides which are designed to be capable of hybridizing to abutting sequences of a single strand of a target. One of the oligonucleotides is biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., *Proc. Natl. Acad. Sci. (U.S.A.)* 87:8923–8927 (1990)). In this method, PCR is used to achieve the exponential amplification of target DNA, which is then detected using OLA. In addition to requiring multiple, and separate processing steps, one problem associated with such combinations is that they inherit all of the problems associated with PCR and OLA.

Boyce-Jacino et al. have described a method for sequencing a polynucleotide using nested GBA (U.S. patent application Ser. No. 08/616,906, herein incorporated by reference. In that method, an array of nested primer oligonucleotides is immobilized to a solid support. A target nucleic molecule is hybridized to the array of nested primer oligonucleotides and the hybridized array is sequenced using GBA.

Pastinen, T. et al. describes a method for the multiplex detection of mutations wherein the mutations are detected by extending immobilized primers, that anneal to the template sequences immediately adjacent to the mutant nucleotide positions, with a single labeled dideoxynucleotide using a DNA polymerase. Pastinen, T. et al., *Genome Res.* 7:606–614 (1997). In this method, the oligonucleotide arrays were prepared by coupling one primer per mutation to be detected on a small glass area. Pastinen, T. et al. has also described a method to detect multiple single nucleotide polymorphisms in an undivided sample. Pastinen, T. et al., *Clin. Chem.* 42:13191–1397 (1996). According to this method, the amplified DNA templates are first captured onto a manifold and then, with multiple minsequencing primers, single nucleotide extension reactions are carried out simultaneously with fluorescently labeled dideoxynucleotides.

Jalanko, A. et al. applied the solid-phase minisequencing method to the detection of a mutation causing cystic fibrosis. Jalanko, A. et al., *Clin. Chem.* 38:39–43 (1992). In the method of Jalanko et al., an amplified DNA molecule which is biotinylated at the 5' terminus is bound to a solid phase and denatured. A detection primer, which hybridizes immediately before the mutation, is hybridized to the immobilized single stranded template and elongated with a single, labeled deoxynucleoside residue. Shumaker, J. M. et al. describes another solid phase primer extension method for mutation detection. Shumaker, J. M. et al., *Hum. Mutation* 7:346–354 (1996). In this method, the template DNA was annealed to an oligonucleotide array, extended with $^{32}P$ dNTPs and analyzed with a phosphoimager. The grid position of the oligonculeotide identified the mutation site and the extended base identified the mutation.

Caskey, C. et al. describes a method of analyzing a polynucleotide of interest using one or more sets of consecutive oligonucleotide primers differing within each set by one base at the growing end thereof. Caskey, C. et al., WO 95/00669. The oligonucleotide primers are extended with a chain terminating nucleotide and the identity of each terminating nucleotide is determined.

Existing methods for de novo sequencing on solid phase arrays consist primarily of hybridization of template nucleic acids to arrayed primers containing combinatorial sequences which hybridize to complementary sequences on the template strand. These methods combine the capture of the template with the specific hybridization function. Therefore, these primers are typically at least 12 bases in length (which contains over 16,000,000 different sequence combinations). Obviously, these arrays are very complex and time consuming to both construct and screen.

Therefore, it would be preferable to design a primer array system which separates the template capture function form the specific hybridization function of the arrayed primers to thereby simplify the array analysis. The present invention describes such a primer array system.

SUMMARY OF THE INVENTION

The present invention describes a novel nucleic acid sequencing reagent which consists of a capture moiety, a spacer region and a sequence specific hybridizing region of 4–8 bases. Preferably, the nucleic acid sequencing reagent is arranged into a nested array. This array configuration can then be used to sequence a given template without prior knowledge (de novo) of the wild type or expected sequence in conjunction with primer extension in the presence of a labeled chain terminating nucleotide.

The sequencing reagent of the present invention comprises:

i) a capture moiety which can form a stable complex with a region of a template nucleic acid molecule;

ii) a spacer region; and iii) a sequence specific hybridizing region, wherein the sequence specific region comprises 4–8 bases which can hybridize to a complementary sequence on the template nucleic acid molecule.

Preferably, the sequencing reagent of the present invention further comprises a modification for attachment of the reagent to a solid surface. More preferably, the modification is at the 5' terminus of the reagent.

Preferably, the sequencing reagents of the present invention are immobilized to a solid surface in an orderly array. More preferably, a plurality of unique sequencing reagents are organized into a combinatorial array. Such an array can be used to sequence a template nucleic acid even without prior knowledge (de novo) of the wild type or "expected" sequence.

Thus, the present invention also describes a method of sequencing a template nucleic acid molecule on a combinatorial array. The sequencing method employs the following steps:

A) immobilizing a sequencing reagent individually or in a group to a solid surface in a spatially distinct fashion, wherein the sequencing reagent comprises:
   i) a capture moiety which can form a stable complex with a region of a template nucleic acid molecule;
   ii) a spacer region; and
   iii) a sequence specific hybridizing region, wherein the sequence specific region comprises 4–8 bases which can hybridize to a complementary sequence on the template nucleic acid molecule;

B) hybridizing the template nucleic acid to the capture moiety of the sequencing reagent;

C) hybridizing the sequence specific hybridizing region to a complementary region on the template strand;

D) extending the hybridized sequence specific region by a polymerase with a labeled chain terminating nucleotide;

E) determining the identity of the extended sequence by detecting the incorporated labeled chain terminating nucleotide.

DESCRIPTION OF THE PREFERRED EMBODIMENTS

I. SYNTHESIS OF A SOLID PHASE ARRAY OF COMBINATORIAL OLIGONUCLEOTIDES

The inclusion of a large number of oligonucleotide probes within a single array greatly reduces the cost of their synthesis and allows thousands of hybridizations to be carried out simultaneously.

A. Synthesis of a Sequencing Reagent

There are two preferred methods to make a nucleic acid array: one is to synthesize the specific oligonucleotide sequences directly onto the solid-phase (in situ) in the desired pattern (Southern, et al., *Nucl. Acids Res.* 22:1368–1373 (1994); Maskos, et al., *Nucl. Acids Res.* 20:1679–1684 (1992); and Pease, et al., *Proc. Natl. Aced. Sci.* 91:5022–5026 (1994); all of which are herein incorporated by reference) and the other is to pre-synthesize the oligonucleotides on an automated DNA synthesizer (such as an ABI 392) and then attach the oligonucleotides onto the solid-phase at specific locations (Lamture, et al., *Nucl. Acids Res.* 22:2121–2125 (1994) and Smith, et al., *Nucl. Acids Res.* 22:5456–5465 (1994) both of which are herein incorporated by reference). In the first method, the efficiency of the coupling step of each base will affect the quality and integrity of the nucleic acid molecule array. This method generally yields a large percentage of undesired incomplete (shortened) sequences which can create problems in the analysis step and effect the integrity of the analysis. Thus, the quality and integrity of an array synthesized according to the first method is inversely proportional to the length of the nucleic acid molecule. Specifically, the synthesis of longer oligonucleotides results in a higher percentage of incomplete, shortened sequences.

A second, more preferred, method for nucleic acid array synthesis utilizes an automated DNA synthesizer for DNA synthesis. Oligonucleotides are synthesized using standard phosphoramidite chemistry. Matteucci, M. D. et al., *J. Amer. Chem. Soc.* 103:3185–3191 (1981), herein incorporated by reference. Preferably, a segmented synthesis strategy is used to simultaneously synthesize large numbers of oligonucleotides. Beattie, K. L. et al., *Appl. Biochem. Biotechnol.* 10:510–521 (1988); and Beattie, K. L., et al., *Nature* 352:548–549 (1991), both of which are herein incorporated by reference. The controlled chemistry of an automated DNA synthesizer allows for the synthesis of longer, higher quality DNA molecules than is possible with the first method. Also, the nucleic acid molecules synthesized according to the second method can be purified prior to the coupling step. Therefore, the quality of the nucleic acid molecule array can be expected to be much higher than the quality of the nucleic acid array of the first method.

Figure 1:
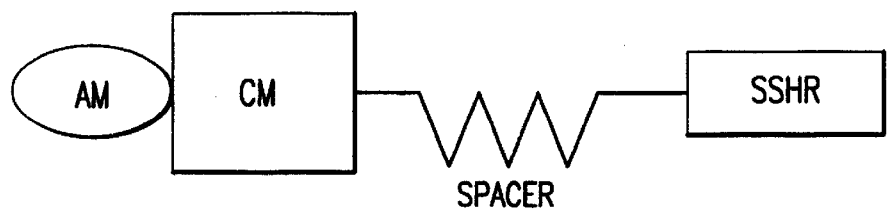
FIG. 1 is a diagrammatic of the structure of the sequencing primer described in the present invention.

The sequencing array reagent of the present invention is designed for use as part of a combinatorial array for primer extension-based sequencing of template nucleic acids. The preferred embodiment of the sequencing primer is illustrated below in FIG. 1.

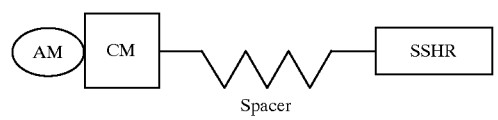

FIG.1

Under one preferred embodiment, an attachment moiety (AM) is coupled to the 5' terminus of the sequencing reagent. The attachment moiety permits attachment of the sequencing reagent to the solid surface. However, the attachment moiety is not necessary to practice the present invention. Especially when the sequencing reagent is non-specifically attached to the solid surface. Under one of the preferred embodiments, the sequencing reagent is non-specifically attached to the solid surface. The sequencing reagent can be non-specifically attached to the solid surface by means of a cationic agent, such as octyl-dimethylamine HCL or NaCl. Alternatively, the sequencing reagent can be non-specifically attached to a charged surface, such as an amino modified solid surface.

Under another preferred embodiment, the sequencing reagent is specifically attached to the solid surface.

Preferably, the specific attachment of the sequencing reagent is by means of a reversible bond.

Under one preferred embodiment, the sequencing reagent can be specifically attached to the solid surface by means of a non-covalent bond. For example, a biotin or iminobiotin labeled oligonucleotide may be immobilized to an avidin or strepavidin coated solid surface. Alternatively, a haptenated oligonucleotide may be immobilized to an antibody coated solid surface. However, it is to be understood that other ligand receptor interactions are suitable for use in the present invention.

Under another preferred embodiment, the sequencing reagent is specifically attached to the solid surface by means of a covalent bond. Preferably, the covalent bond is a disulfide bond. Additional embodiments for attaching the sequencing reagent to the solid surface are discussed with respect to the capture moiety. It is intended that the embodiments for immobilizing a nucleotide to a solid surface discussed with respect to the capture moiety can be applied to immobilize the present sequencing nucleotides to a solid surface.

Modifications suitable for use in the present invention include the incorporation of an amino, thiol, disulfide, biotin, etc. group at the 5' terminus of the sequencing primer. This modification can either be done either at the time the sequencing reagent is synthesized or after the sequencing primer has been synthesized.

The "capture" moiety (CM) of the sequencing reagent is a moiety which can form a stable complex with a region of the template nucleic acid. The capture moiety can be at or near the 5' or 3' terminus of the sequencing reagent.

The capture moiety can be either a DNA, RNA or PNA (protein nucleic acid) sequence. The nucleic acid sequence may also contain modified bases. For example, a RNA sequence may contain 2'-O-methoxy RNA and a DNA sequence may contain 5-Me-dC, pdC, pdU, or 2-amino-dA. Under another embodiment, the nucleic acid sequence may contain a modified backbone wherein the backbone is modified with phosphorothioate, phosphordithioate, methylposphonate or H-phosphonate.

Under another preferred embodiment, the capture moiety may be biotin, iminobiotin, avidin, strepavidin, antibody, hapten, receptor, ligand, or charged base. Receptors and ligands suitable for use in the present invention include, but are not limited to, protein A, protein G, Fc portion of an antibody, or Fc receptor.

The capture moiety can form a stable complex with the region of template nucleic acid by means of a disulfide bond, a covalent ether or thioether linkage via an epoxy, UV cross-linkage, a condensation reaction with a carbodiimide, a bromoacetyl/thiol linkage to a thioester, a crosslinkage with a bi-functional group or a complex between thiol and gold. Bi-functional crosslinking reagents suitable for use in the present invention include, but are not limited to, an imidiester, N-hydroxysuccinimidyl ester, malemide, alkyl halide, aryl halide, alpha-haloacyl and pyridyl disulfide. The capture moiety can also be covalently attached by means of a labeling group. Labeling groups suitable for use in the present invention include, but are not limited to, amino, sulfhydryl, disulfide, phosphate, thiophosphate, dithiophosphate and psoralen groups.

The capture moiety can also exist as a separate molecule that is co-attached to the solid phase and effectively brings the template into close proximity to the sequence specific hybridizing portion of the reagent (SSHR).

In one of the preferred embodiments, the capture moiety is a sequence of 8–24 C bases which can hybridize to a sequence of 8–24 G bases incorporated on the template strand. In another preferred embodiment, the capture moiety can be a specific sequence complementary to a PCR primer, or portion thereof, used to amplify a region of the template strand. For example, the capture moiety is a sequence complementary to a restriction site found within the PCR primer. Alternatively, the PCR primer hybridizes to a promoter site and thus, the capture sequence is the same sequence as a promoter site. PCR primer design is well known to those of skill in the art and it is appreciated that the capture sequence can be complementary to a PCR primer, portion thereof or modification thereof.

The efficiency of hybridization and the thermal stability of hybrids formed between the target nucleic acid and a short oligonucleotide probe depends strongly on the nucleotide sequence of the probe and the stringency of the reaction conditions. Conner, B. J. et al., *Proc. Natl. Acad. Sci. (U.S.A.)* 80:278–282 (1983), herein incorporated by reference.

The spacer region is preferably at least 10 nm in length, more preferable 10–100 nm in length. However, the spacer region can also be $\geq$100 nm in length. Spacer regions suitable for use in the present invention include, but are not limited to, DNA or RNA sequences, PNA sequences, polyethylene glycol groups, or other chemical spacer arms. The spacer region can also consist of analogs of DNA, RNA and PNA. Preferably, the spacer region consists of a random sequence of bases. However, the spacer region can also consist of a sequence of pseudo-random or non-random bases. Preferably, the spacer region is designed to minimize template independent noise. Template independent noise is the result of signal detection independent (in the absence) of template. Under one embodiment, a spacer region is additionally placed in between the capture moiety and the attachment moiety.

The sequence specific hybridizing region (SSHR) of the reagent consists of 4–8 specific bases which can hybridize to complementary sequences on the template strand and can be extended by a polymerase with one or more labeled non-extendible or chain terminating nucleotides. More preferably, SSHR consists of 4–6 specific bases which can hybridize to complementary sequences on the template strand. Preferably, the non-extendible or chain terminating nucleotides of the present invention are ddNTPs.

In addition to dideoxynucleotides, 3'-phosphate modified oligonucleotides, which are complementary to a template nucleic acid molecule and effectively block DNA polymerization, can be used in the present invention. Kornberg et al., In: *DNA Replication*, 2nd Edition, Kornberg et al. eds. (W. H. Freeman & Co., San Fransisco) pp. 408, 446–449 (1992), herein incorporated by reference. Alternatively, a nucleotide analog, such as a fructose based nucleotide analog or a chemically modified purine or pyrimidine that retains the ability to specifically base pair with naturally occurring nucleotides may be used to block DNA polymerization. A variety of 3'-substituted nucleotides (Antrazhev, *Bioorg. Khim.* 13:1045–52 (1987); Chidgeavadze, Z. G. et al., *Biochim. Biophys. Acta* 868:145–52 (1986); Chidzhacadze et al., *Mol. Biol.* (Mosk.) 23:1732–42 (1989)), such as azido- (Mitsuya et al., *Proc. Natl. Acad. Sci. (USA)* 83:1191 (1986), mercapto- (Yuzhakov et al., *FEBS Letters* 306:185–88 (1992), amino- (Herrein et al., *Helvetica Chimica Acta* 77:586–96 (1994), and fluoro- (Chidgeavadze, Z. G. et al., *FEBS Letters* 183:275–8 (1985) substituted nucleotides, which have been reported to terminate DNA synthesis, can be used in the present invention (all of which are herein incorporated by reference).

In the present invention, the non-extendible nucleotide can be detectably labeled, preferably with a florescent molecule or haptenated dideoxy-nucleotide. Alternatively, the non-extendible nucleotide can be detected using delayed extraction MALDI-TOF mass spectrometry. Haff, L. A. et al., *Genome Methods* 7:378–388 (1997), herein incorporated by reference. MALDI-TOF mass spectrometry is capable of determining the identity of the incorporated non-extendible nucleotide by the change in mass of the extended primer.

The use of a fluorescently labeled non-extendible nucleotide is more preferable. Other labels suitable for use in the present invention include, but are not limited to, biotin, iminobiotin, an antigen, a cofactor, dinitrophenol, lipoic acid, an olefinic compound, a detectable polypeptide, a molecule that is electron rich, an enzyme capable of generating a detectable signal and a radioactive isotope. The preferred radioactive isotopes are $^{32}P$, $^{35}S$, $^{14}C$, and $^{125}I$. Florescent molecules suitable for the present invention include, but are not limited to, fluorescein, rhodamine, texas red, FAM, JOE, TAMRA, ROX, HEX, TET, Cy3, Cy3.5, Cy5, Cy5.5, IRD40, IRD41 and BODIPY. As used herein, "FAM" shall refer to 5-carboxy-fluorescein, "JOE" shall refer to 2',7'-dimethoxy-4',5'-dichloro-6-carboxy-fluorescein, "TAMRA" shall refer to N,N,N',N'-tetramethyl-6-carboxy-rhodamine, "ROX" shall refer to 6-carboxy-X-rhodamine. Electron rich indicator molecules suitable for the present invention include, but are not limited to, ferritin, hemocyanin and colloidal gold. Alternatively, the polypeptide may be indirectly detected by specifically complexing a first group to the polypeptide. A second group, covalently linked to an indicator molecule, which has affinity for the first group could be used to detect the polypeptide. In such an embodiment, compounds suitable for use as a first group include, but are not limited to, avidin and strepavidin. Compounds suitable for use as a second group include, but are not limited to, biotin and iminobiotin.

One of the advantages of this invention, compared to conventional methods, is that four fold fewer primers are required to sequence a template of a given complexity. The addition of a single, identifiable base through the primer extension step effectively increases the length of each hybridized primer by one. Thus, a 5 mer which has 1024 different sequence combinations) is extended to form a 6 mer (which has 4096 different sequence combinations) by the polymerase. Therefore, primer extension sequencing on an array of 5 mers will be as effective at sequencing a complex template as an array of 6 mers by hybridization sequencing alone.

Another advantage of the present invention is that fewer specific bases are utilized to analyze the template sequence by separation of the template capture and sequence determination functions. For example, the duplex formed by four specific bases is stable enough to prime the extension reaction of a polymerase at room temperature even though it is not stable enough to efficiently and specifically capture the template strand by preventing it from washing off during the removal of any unhybridized template.

B. The Immobilization of Pre-Synthesized Nucleic Acid Molecules to a Solid Phase Recently, several methods have been proposed as suitable for immobilizing an oligonucleotide to a solid support. Holmstrom, K. et al., for example, exploit the affinity of biotin for avidin and streptavidin, and immobilize biotinylated nucleic acid molecules to avidin/streptavidin coated supports (Holmstrom, K. et al., *Anal. Biochem.* 209:278–283 (1993), herein incorporated by reference). Another method requires the pre-coating of the polystyrene or glass solid phases with poly-L-Lys or poly L-Lys, Phe, followed by the covalent attachment of either amino- or sulfhydryl-modified oligonucleotides using bi-functional crosslinking reagents. Both methods require the use of modified oligonucleotides as well as a pretreatment of the solid phase (Running, J. A. et al., *BioTechniques* 8:276–277 (1990); Newton, C. R. et al. *Nucleic Acids Res.* 21:1155–1162 (1993), both of which are herein incorporated by reference).

Kawai, S. et al. describes an alternative method in which short oligonucleotide probes were ligated together to form multimers and these were ligated into a phagemid vector (Kawai, S. et al., *Anal. Biochem.* 209:63–69 (1993), herein incorporated by reference). The oligonucleotides were immobilized onto polystyrene plates and fixed by UV irradiation at 254 nm. A method for the direct covalent attachment of short, 5'-phosphorylated primers to chemically modified polystyrene plates ("Covalink" plates, Nunc) has also been proposed by Rasmussen, S. R. et al. (*Anal. Biochem.* 198:138–142 (1991), herein incorporated by reference). The covalent bond between the modified oligonucleotide and the solid phase surface is created by a condensation reaction with a water-soluble carbodiimide. The Rasmussen method claims a predominantly 5'-attachment of the oligonucleotides via their 5'-phosphates; however, it requires the use of specially prepared, expensive plates.

Maskos, U. et al. describes a method to synthesize oligonucleotides directly onto a glass support (Maskos, U. et al., *Nucl. Acids Res.* 20:1679–1684 (1992), herein incorporated by reference). According to this method, a flexible linker with a primary hydroxyl group is bound to the solid support via a glycidoxypropyl silane, wherein the primary hydroxyl group serves as the starting point for the oligonucleotide synthesis. The disadvantages of this method are that the reaction is not reversible and the oligonucleotides leak from the solid surface during manipulation.

Covalent disulfide bonds have been previously used to immobilize both proteins and oligonucleotides. Carlsson, J. et al., (*Biotech. Applied Biochem.* 14:114–120 (1991)) discloses a method for the reversible immobilization of thiolated proteins and peptides to an agarose bead by means of a disulfide bond. In that method, the disulfide bond is formed between a thiol containing protein and a thiol-derivatized agarose bead. The reference also discloses that the disulfide bond is reversible in the presence of an excess of dithiothreitol. Chu, B. C. F. et al. (*Nucleic Acids Res.* 16: 3671–3691 (1988)) discloses a method for coupling oligonucleotides to nucleic acids or proteins via cleaveable disulfide bonds. Prior to the coupling reaction, the oligonucleotides are modified by adding a cystamine group to the 5' phosphate by means of a phosphoramadite bond. Sliwkowski, M. X. et al (*Biochem. J.* 209: 731–739 (1983)) discloses a method of covalent chromatography wherein proteins are immobilized to cysteinylsuccinimidoproyl glass beads through reversible disulfide bond interaction.

Fahy, E. et al. (*Nucleic Acids Res.* 21: 1819–1826 (1993)) describes the synthesis of 5'-bromacetyl and 5'-thiol oligonculeotide derivatives and the covalent immobilization of these oligonucleotide derivatives via thioester bonds to sulfhydryl- and bromacetyl-modified polyacrylamide supports. The disadvantage of this method is that the covalent bond is not reversible.

Anderson et al. describes novel method for immobilizing nucleic acid molecules to a solid-phase by means of a reversible, covalent disulfide bond (Ser. No. 08/812,010, filed on Mar. 5, 1997, herein incorporated by reference). In that method, a disulfide bond is formed between a thiol or disulfide containing nucleic acid molecule and a mercaptosilane coated solid surface. Shi et al. (Ser. No. 08/870,010, herein incorporated by reference), describes a novel method for immobilizing nucleic acid molecules to a solid phase by means of a covalent ether or thioether linkage. These simple, two-step methods have the specificity and efficiency needed to prepare DNA arrays.

Although all of the above described methods can be used to immobilize the sequencing reagent of the present invention to the solid support, the preferred embodiments are disclosed by Anderson et al. and Shi et al. An additional preferred embodiment for immobilizing the sequencing reagent of the present invention is to immobilize biotinylated nucleic acid molecules to avidin/streptavidin coated supports as disclosed by Holmstrom, K. et al., *Anal. Biochem.* 209:278–283 (1993).

Although any of a variety of glass or plastic solid supports can be used in accordance with the methods of the present invention, plastic is the preferred solid support. Preferably, the solid support can be fashioned as a 96-well or 384-well plate. However, the support can also be fashioned as a bead, dipstick, test tube, pin, membrane, channel, capillary tube, column, or as an array of pins or glass fibers. Preferably, the plastic support is a form of polystyrene plastic. Alternatively, the solid support can be glass, preferably in the form of a microscope slide, coverslip, a capillary tube, a glass bead or a channel. The solid support can also be a glass plate, a quartz wafer, a nylon or nitrocellulose membrane or a silicon wafer.

Currently, 96-well polystyrene plates are widely used in solid-phase immunoassays, and several PCR product detection methods that use plates as a solid support have been described. The most specific of these methods require the immobilization of a suitable oligonucleotide probe into the microtiter wells followed by the capture of the PCR product by hybridization and colorimetric detection of a suitable hapten.

C. Array Formation

The sequencing reagents of the present invention are intended to be made into an array. As used herein, an array is an orderly arrangement of sequencing reagents, as in a matrix of rows and columns or spatially addressable or separable arrangement such as with coated beads. Preferably, the array is an array of permutations of the hybridization domains, such as all possible 4 mers, 5 mers, 6 mers, 7 mers, 8 mers or combinations thereof. By using an array of nested sequencing reagents, it is possible to determine the sequence of the target nucleic acid. As used herein, a nested array is an array of reagents whose sequence specific hybridization regions sequentially overlap in sequence.

With an automated delivery system, such as a Hamilton robot or ink-jet printing method, it is possible to form a very complex array of oligonucleotide probes on a solid support, in particular an epoxysilane, mercaptosilane or disulfidesilane coated solid support. Such methods can deliver nano to pico-liter size droplets with sub-millimeter spacing. Because the aqueous beads are extremely well defined, it is possible to create an array with an extremely high density of oligonucleotide probes. Thus, it is possible to create arrays having greater than about 10,000 probe droplets/cm$^2$. Such arrays can be assembled through the use of a robotic liquid dispenser (such as an ink-jet printing device controlled by a piezoelectric droplet generator) such that each nucleic acid molecule occupies a spot of more than about 10 microns, preferably more than 25 microns in diameter and each nucleic acid spot is spaced no closer, center to center, than the average spot diameter. Methods and apparatuses for dispensing small amount of fluids using such ink-jet printing techniques and piezoelectric ink-jet depositions have been previously described by Wallace, D. B. et al. (U.S. Pat. No. 4,812,856), Hayes, D. J. et al. (U.S. Pat. No. 5,053,100), and Hayes, D. J. et al. (*BioTechniques*, June, 1994), all of which are herein incorporated by reference.

Under one embodiment, the array can be constructed using the method of Fodor, S. P. et al. (U.S. Pat. No. 5,445,934). Fodor et al. describes a method for constructing an array onto a solid surface wherein the surface is covered with a photo-removable group. Selected regions of the substrate surface are exposed to light to as to activate the selected regions. A monomer, which also contains a photo-removable group, is provieded to the substrate surface to bind to the selected area. The process is repeated to create an array.

Under another preferred embodiment, the array can be created by means of a "gene pen". A "gene pen", as used herein, refers to a mechanical apparatus comprising a reservoir for a reagent solution connected to a printing tip. The printing tip further comprises a means for mechanically controlling the solution flow. Under one embodiment, a multiplicity of "gene pens" or printing tips may be tightly clustered together into an array, with each tip connected to a separate reagent reservoir. Under another embodiment, discrete "gene pens" may be contained in an indexing turntable and printed individually. Typically, the solid surface is pretreated to enable covalent or non-covalent attachment of the reagents to the solid surface. Preferably, the printing tip is a porous pad.

Alternatively, the array can be created with a manual delivery system, such as a pipetman. Because these arrays are created with a manual delivery system, these arrays will not be as complex as those created with an automated delivery system. Arrays created with a manual delivery system will typically be spaced, center to center, $\geq 2$ mm apart. Preferably, arrays created with a manual delivery system will be created in a 96-well or 384-well plate. Therefore, depending on the delivery system employed, it is possible to create arrays spaced, center to center, with $\geq 2$ mm spacing, 0.5–2 mm spacing, 50–500 $\mu$m spacing or $\leq 50$ $\mu$m spacing.

II. THE USE OF IMMOBILIZED NUCLEIC ACID MOLECULES

Immobilized nucleic acid molecules, and more preferably, immobilized oligonucleotides, make an ideal diagnostic tool. Specifically, their versatility and simplicity make them ideal diagnostic tools for the detection of infectious and genetic diseases, mutation analysis, etc.

A. Generation of Single Stranded Nucleic Acid Molecules

The methods of the present invention do not require that the target nucleic acid contain only one of its natural two strands. Thus, the methods of the present invention may be practiced on either double-stranded DNA, or on single-stranded DNA obtained by, for example, alkali treatment of native DNA. The presence of the unused (non-template) strand does not affect the reaction.

Where desired, however, any of a variety of methods can be used to eliminate one of the two natural stands of the target DNA molecule from the reaction. Single-stranded DNA molecules may be produced using the single-stranded DNA bacteriophage M13 (Messing, J. et al., *Meth. Enzymol.* 101:20 (1983); see also Sambrook, J. et al., In: *Molecular Cloning: A Laboratory Manual*, Cold Spring Harbor Laboratory Press, Cold Spring Harbor, N.Y. (1989), both of which are herein incorporated by reference).

Several alternative methods can be used to generate single-stranded DNA molecules. Gyllensten, U. et al. (*Proc. Natl. Acad. Sci.* (*U.S.A.*) 85:7652–7656 (1988) and Mihovilovic, M. et al. (*BioTechniques* 7:14 (1989)) describe a method, termed "asymmetric PCR," in which the standard "PCR" method is conducted using primers that are present in different molar concentrations. Higuchi, R. G. et al. (*Nucleic Acids Res.* 17:5865 (1985)) exemplifies an additional method for generating single-stranded amplification products. The method entails phosphorylating the 5'-terminus of one strand of a double-stranded amplification product, and then permitting a 5'→3' exonuclease to preferentially degrade the phosphorylated strand.

Other methods have also exploited the nuclease resistant properties of phosphorothioate derivatives in order to generate single-stranded DNA molecules (Benkovic et al., U.S. Pat. No. 4,521,509); Sayers, J. R. et al. (*Nucl. Acids Res.* 16:791–802 (1988); Eckstein, F. et al., *Biochemistry* 15:1685–1691 (1976); and Ott, J. et al., *Biochemistry* 26:8237–8241 (1987)).

Most preferably, such single-stranded molecules will be produced using the methods described by Nikiforov, T. (commonly assigned U.S. Pat. No. 5,518,900, herein incorporated by reference). In brief, these methods employ nuclease resistant nucleotide derivatives, and incorporate such derivatives, by chemical synthesis or enzymatic means, into primer molecules, or their extension products, in place of naturally occurring nucleotides.

Suitable nucleotide derivatives include derivatives in which one or two of the non-bridging oxygen molecules of the phosphate moiety of a nucleotide has been replaced with a sulfur-containing group (especially a phosphorothioate), an alkyl group (especially a methyl or ethyl alkyl group), a nitrogen-containing group (especially an amine), and/or a selenium-containing group, etc. Phosphorothioate deoxyribonucleotide or ribo-nucleotide derivatives are the most preferred nucleotide derivatives. Methods of producing and using such phosphorothioate derivatives are disclosed by Nikiforov, T. (U.S. Pat. No. 5,518,900).

B. GBA™ Genetic Bit Analysis

The methods of the present invention may also be used to immobilize oligonucleotides that can be used in the GBA™ Genetic Bit Analysis (Goelet, P. et al., PCT Application No. 92/15712, herein incorporated by reference). GBA™ Genetic Bit Analysis describes a solid-phase method for the typing of single-nucleotide polymorphisms. Oligonucleotides having a defined sequence complementary to a region that lies immediately proximal or distal to the variable nucleotide of a polymorphism would thus be provided to a polystyrene microtiter well or glass plate, and incubated with a salt, in accordance with the above-described methods.

The immobilized primer is then incubated in the presence of a DNA molecule (preferably a genomic DNA molecule) having a single nucleotide polymorphism whose immediately 3'-distal sequence is complementary to that of the immobilized primer. Preferably, such incubation occurs in the complete absence of any dNTP (i.e., DATP, dCTP, dGTP, or dTTP), but only in the presence of one or more chain terminating nucleotide derivatives (such as a dideoxynucleotide derivatives), and under conditions sufficient to permit the incorporation of such a derivative onto the 3'-terminus of the primer. As will be appreciated, where the polymorphic site is such that only two or three alleles exist (such that only two or three species of ddNTPs, respectively, could be incorporated into the primer extension product), the presence of unusable nucleotide triphosphate(s) in the reaction is immaterial. In consequence of the incubation, and the use of only chain terminating nucleotide derivatives, a single dideoxynucleotide is added to the 3'-terminus of the primer. The identity of that added nucleotide is determined by, and is complementary to, the nucleotide of the polymorphic site of the polymorphism.

Using the method described in the present invention, oligonucleotide primers can be immobilized on solid phases such as polystyrene or glass, hybridized to PCR-derived, single-stranded templates, and subjected to enzymatic extension at their 3'-ends by a single, labeled ddNTP. The nature of the incorporated ddNTP is determined by the nucleotide that is located in the opposite strand (the polymorphic nucleotide). This assay can be conveniently carried out both in polystyrene ELISA plates, or on glass slides.

In this embodiment, the nucleotide of the polymorphic site is thus determined by assaying which of the set of labeled nucleotides has been incorporated onto the 3'-terminus of the bound oligonucleotide by a primer-dependent polymerase. Most preferably, where multiple dideoxynucleotide derivatives are simultaneously employed, different labels will be used to permit the differential determination of the identity of the incorporated dideoxynucleotide derivative.

By using an array of nested sequencing primers, it is possible to modify the GBA method for use in the present invention to sequence large segments of a template nucleic acid molecule simultaneously. By aligning the extension products of the nested primers, one of skill in the art can determine the sequence of the unknown target sequence. The general strategy of sequencing by aligning nested primers is disclosed by Sapolsky, R. J. et al., *Genomics* 33:445–456 (1993), Pease, A. C. et al., *Proc. natl. Acad. Sci.* (*U.S.A.*) 91:5022–5026 (1994) and Bains, W., *GATA* 10:84–93 (1993), all of which are herein incorporated by reference.

C. Ligase-Mediated GBA™

The methods and reagents of the present invention can also be used in concert with a polymerase/ligase mediated polymorphic interrogation assay. This assay, termed ligase-mediated GBA™ genetic bit analysis, is a more specific version of the GBA™ genetic bit analysis assay. The additional specificity arises from the addition of a second hybridization step and a ligation step.

In this assay, two oligonucleotides are employed. The first oligonucleotide is a primer that is complementary to the immediately 3'-distal invariant sequence of the polymorphism. The 3'-end of the oligonucleotide is attached to the plate. A second linker oligonucleotide is complementary to the 5'-proximal sequence of the polymorphism being analyzed, but is incapable of hybridizing to the first oligonucleotide. The second linker oligonucleotide is phosphorylated at both its 3' and 5' ends.

These oligonucleotides are incubated in the presence of DNA containing the single nucleotide polymorphism that is to be analyzed, and at least one 2'-deoxynucleotide 5'-triphosphate. The incubation reaction further includes a DNA polymerase and a DNA ligase. The tethered and soluble oligonucleotides are thus capable of hybridizing to the same strand of the target molecule under analysis. The sequence considerations cause the two oligonucleotides to hybridize to the proximal and distal sequences of the single nucleotide polymorphism (SNP) that flank the variable nucleotide of the polymorphism, and to be separated by a single nucleotide at the precise position of the variability.

The presence of a polymerase and the 2'-deoxynucleotide 5'-triphosphate complementary to the nucleotide present in the variable site of the polymorphism permits the extended primer to be ligated to the bound oligonucleotide, thereby immobilizing the primer. The identity of the polymorphic site that was opposite the single nucleotide can then be determined by any of several means. In a preferred embodiment, the 2'-deoxynucleotide 5'-triphosphate of the reaction is labeled, and its detection thus reveals the identity of the complementary nucleotide of the polymorphic site. Several different 2'-deoxynucleotide 5'-triphosphates may be present, each differentially labeled. Alternatively, separate reactions can be conducted, each with a different 2'-deoxynucleotide 5'-triphosphate. In an alternative sub-embodiment, the 2'-deoxynucleotide 5'-triphosphates are unlabeled, and the soluble oligonucleotide is labeled. In this embodiment, the primer that is extended is immobilized on the polystyrene. Separate reactions are conducted, each using a different unlabeled 2'-deoxynucleotide 5'-triphosphate.

Having now generally described the invention, the same will be more readily understood through reference to the following examples which are provided by way of illustration and are not intended to be limiting on the present invention.

EXAMPLE 1

COUPLING OF THE SEQUENCING REAGENT TO THE SOLID SUPPORT BY MEANS OF A DISULFIDE EXCHANGE REACTION

The general chemistry of the thiol-disulfide exchange reaction has been previously described by Ryden, L. et al., herein incorporated by reference. (In: Jansosn, J. et al., eds. *Protein Purification: Principles, High Resolution Methods, and Application*, VHC Publishers, Inc., New York, N.Y. (1989)).

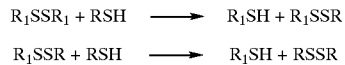

Attachment of the 5'- or 3'-disulfide modified oligonucleotide is obtained by a two step process of silane treatment and oligonucleotide binding. Initially, the glass slides are etched overnight in 25% aqueous ammonium hydroxide and then rinsed sequentially with milliQ water and 95% ethanol. The glass slides are then treated for 30 minutes with 3-mercapto-proyl-trimethoxysilane (MPTS) in an acidic buffer of aqueous ethanol (95% ethanol, pH 4.5). The slides are then cured for at least 48 hours under a dry inert gas, such as $Ar_2$ or $N_2$.

The cured slides are treated with 5'-disulfide modified sequencing reagents in a carbonate buffer (500 mM, pH 9.0) for 2 hours at room temperature. The disulfide reaction between the RS group on the sequencing reagent and the available thiol of the mercaptosilane yields a disulfide bond between the sequencing reagent and the silane layer.

Experimental results indicate that the attachment efficiency of this attachment chemistry is very high. This method is very specific (at least 80 to 90% specificity) and provides a very high density of sequencing reagent attachment ($10^5$ molecules/mm$^2$).

EXAMPLE 2

COUPLING OF THE SEQUENCING REAGENT TO THE SOLID SUPPORT BY MEANS OF A DISULFIDE FORMATION REACTION

In a second embodiment, the coupling reaction is accomplished by means of a disulfide formation reaction. This method is used to attach sequencing reagents to a glass slide by coupling 5'-sulfhydyl modified sequencing reagents to sulfhydryl groups of the mercaptosilane coated surface.

The glass slides are initially coated with mercaptosilane to introduce sulfhydyl groups onto the surface following the protocol detailed above. 5'-sulfhydryl modified sequencing reagents are obtained by treating the disulfide modified sequencing reagent with dithiolthreitol (0.04M in 0.17M phosphate buffer, pH 8.0) at room temperature overnight. Then, the 5'-sulfhydryl modified sequencing reagents (at a concentration greater than 2 μm) are exposed to the mercaptosilane surface in a carbonate buffer (500 mM, pH 9.0) for 2 hours at room temperature. The formation of disulfide bonds between the surface mercaptosilane and the 5'-sulfhydryl groups result in the covalent attachment of the sequencing reagents.

EXAMPLE 3

PASSIVE ADSORPTION OF THE SEQUENCING REAGENT TO THE SOLID SUPPORT

Several methods can be used to non-specifically adsorb sequencing reagents to solid supports such as 96-well polystyrene plates. One such method involves the dilution of the sequencing reagent to a 200 nM concentration in a 50 mM solution of octyl-dimethylamine-HCl (ODA). This solution is then incubated (50 μl/well) in polystyrene 96-well plates. After overnight incubation at 37° C., the plate is washed with 10 mM Tris pH 7.5/150 mM NaCl/0.05% polysorbitan 20 (Tween-20) (herein referred to as "TNTw") to remove excess primer. This method can also work with other cationic agents (instead of ODA) such as cetyl-trimethylammonium chloride and salts such as NaCl.

EXAMPLE 4

PREPARATION OF AN SEQUENCING REAGENT ARRAY WITH AN AUTOMATIC DELIVERY SYSTEM

One method for the automated delivery of the sequencing reagent solution employs an ink-jet printing technique performed by MicroFab Technologies, Inc. (Plano, Tex.). The ink-jet printing technique is used to make arrays of sequencing reagent drops ranging in size from about 125 pl to about 25 nl, with 125 μm to 1 μm between spots.

Alternatively, a Hamilton 2200 automated pipeting robot is used to make arrays of sequencing reagent drops, ranging in size from about 100 nl to about 250 nl, with approximately 0.5–2 μm spacing between dots. As in the ink-jet printing method, a Hamilton robot can be programmed to deliver nanoliter size droplets with sub-millimeter spacing.

EXAMPLE 5

PREPARATION OF SINGLE-STRANDED PCR PRODUCTS

In order to protect one of the strands of the double-stranded PCR product from exonuclease hydrolysis, four phosphorothioate bonds are introduced during synthesis at the 5'-end of one of each pair of the PCR primers. For generation of single-stranded PCR products, following the PCR amplification, T7 gene 6 exonuclease is added to a final concentration of 2 units/µl of PCR reaction. Incubation is for one hour at room temperature. The T7 gene 6 exonuclease can be purchased from USB and diluted in a buffer recommended by the manufacturer. Following the exonuclease treatment, aliquots of the reaction mixtures are withdrawn and analyzed by polyacrylamide gel electrophoresis.

EXAMPLE 6

HYBRIDIZATION OF SINGLE-STRANDED PCR FRAGMENTS TO SEQUENCING REAGENTS IMMOBILIZED IN ELISA PLATES

After the exonuclease treatment, an equal volume of 3 M NaCl, 20 mM EDTA is added to the reaction mixture and 20 µl aliquots of the resulting solution transferred to individual wells containing the appropriate immobilized sequencing reagent molecule. These capture probes are immobilized using 500 mM NaCl. Hybridization is carried out for 30 minutes at room temperature and is followed by washing with TNTw.

EXAMPLE 7

DETERMINING THE SEQUENCE OF A TEMPLATE USING SEQUENCE REAGENTS WITH FIVE SPECIFIC BASES

A sequencing reagent array was immobilized to the surface of a 96 well dish using the passive immobilization method described in Example 3. Hybridization of the single stranded DNA template (SEQ ID NO. 1) was accomplished by dilution of the template to 100 nM in 1.5M NaCl and incubating each well with 30 µl of this mixture at room temperature for 30–60 minutes. The plate was subsequently washed 3 times with TNTw (Tris/NaCl/Tween). Twenty µl of polymerase extension mix containing ddNTPs (1.5 µM each, one of which was fluoroscein labeled/5 mM dithiothreitol (DTT)/7.5 mM sodium isocitrate/5 mM $MnCl_2$/0.04 units per µl of modified Klenow fragment DNA polymerase) and incubated for 5 minutes at room temperature. Following the extension reaction, the plate was washed with TNTw.

The presence of incorporated fluorescein labeled ddNTP was detected by incubation of each well with anti-fluorescein alkaline phosphatase conjugated antibody for 30 minutes. Unattached antibody was removed by washing each well six times with TNTw. Attached antibody was detected by addition of alkaline phosphatase substrate (P-nitrophenyl phosphate) and measuring the optical density of the substrate solution (at 405 nm) after 5–15 minutes.

Table 1 provides the sequence of the sequencing reagents used in the present experiment. The results of the sequencing reaction are depicted in Table 2.

TABLE 1

| SEQ ID | SEQUENCES | Expected Signal |
|---|---|---|
| NO. 1 (template) | 5'-$(G)_{20}$CTAGTGGAAATAGTTTCATGTTCAT-3' | |
| NO. 2 | 5'-$(C)_{18}(N)_8$TTTCC-3' | A |
| NO. 3 | 5'-$(C)_{18}(N)_8$TTCCA-3' | C |
| NO. 4 | 5'-$(C)_{18}(N)_8$TCCAC-3' | T |
| NO. 5 | 5'-$(C)_{18}(N)_8$ATTTC-3' | C |
| NO. 6 | 5'-$(C)_{18}(N)_8$TATTT-3' | C |
| NO. 7 | 5'-$(C)_{18}(N)_8$CTATT-3' | T |
| NO. 8 | 5'-$(C)_{18}(N)_8$ACTAT-3' | T |
| NO. 9 | 5'-$(C)_{18}(N)_8$AACTA-3' | T |
| NO. 10 | 5'-$(C)_{18}(N)_8$AAACT-3' | A |
| NO. 11 | 5'-$(C)_{18}(N)_8$GAAAC-3' | T |
| NO. 12 | 5'-$(C)_{18}(N)_8$TTCC-3' | A |
| NO. 13 | 5'-$(C)_{18}(N)_8$TCCA-3' | T |
| NO. 14 | 5'-$(C)_{18}(N)_8$TCCAC-3' | T |
| NO. 15 | 5'-$(C)_{18}(N)_8$CCAC-3' | T |
| NO. 16 (template) | 5'-$(G)_{20}$TGTGGCCTAGTGGAAATAGTTAA CGCGACTG-3' | |
| NO. 17 | 5'-$(C)_{18}(N)_8$CGCG-3' | T |
| NO. 18 | 5'-$(C)_{18}(N)_7$CCCCGCG | T |
| NO. 19 | 5'-$(C)_{18}(N)_8$GGCC-3' | A |
| NO. 20 | 5'-$(C)_{18}(N)_7$CCCGGCC-3' | A |
| NO. 21 | 5'-$(C)_{18}(N)_8$AGGCC-3' | A |
| NO. 22 | 5'-$(C)_{18}(N)_8$CGGCC-3' | A |
| NO. 23 | 5'-$(C)_{18}(N)_8$GGGCC-3' | A |
| NO. 24 | 5'-$(C)_{18}(N)_8$TGGCC-3' | A |
| NO. 25 | 5'-$(N)_{12}$ACTAT-3' | T |
| NO. 26 | 5'-$(C)_{25}$-3' | |
| NO. 27 | 5'-$(TG)_9(N)_8$ACTAT-3' | T |
| NO. 28 | 5'-$(TG)_9$-3' | |
| NO. 29 (template) | 5'-CTAGTGGAAATAGTTTCAT GTTCAGTGTGT$(G)_{20}$-3' | |
| NO. 30 (template) | 5'-CTAGTGGAAATAGTTTCAT GTTCAGTGTGT-3' | |
| NO. 31 | 5'-$(C)_{18}(N)_8$TATTTCC-3' | A |

TABLE 2

| labeled ddNTP | SEQ ID NO. 8 | SEQ ID NO. 7 | SEQ ID NO. 6 | SEQ ID NO. 5 | SEQ ID NO. 2 | SEQ ID NO. 3 | SEQ ID NO. 5 | Blank |
|---|---|---|---|---|---|---|---|---|
| A | 0.329 | 0.362 | 0.773 | 0.247 | 1.339 | 0.159 | 0.142 | 0.105 |
| A | 0.308 | 0.346 | 0.751 | 0.242 | 1.371 | 0.164 | 0.149 | 0.106 |
| C | 0.163 | 0.176 | 1.393 | 1.213 | 0.133 | 1.584 | 0.114 | 0.114 |
| C | 0.160 | 0.182 | 1.340 | 1.315 | 0.138 | 1.550 | 0.121 | 0.116 |
| G | 0.633 | 0.422 | 0.834 | 0.257 | 0.137 | 0.184 | 0.120 | 0.108 |
| G | 0.628 | 0.390 | 0.720 | 0.249 | 0.135 | 0.174 | 0.120 | 0.103 |
| T | 1.429 | 1.175 | 0.300 | 0.137 | 0.105 | 0.132 | 1.272 | 0.103 |
| T | 1.489 | 1.230 | 0.310 | 0.135 | 0.118 | 0.138 | 1.408 | 0.105 |

Thus, one of skill in the art could determine that the sequence of the template molecule is 5'-TTCCTCA-3'. However, algorithms and software have been developed for sequence reconstruction which are applicable to the methods described herein (Drmanac, R. et al., *J. Biomol. Struc. & Dyn.* 8:1085–1121 (1991); Pevzner, P. A., *J. Biomol. Struc. & Dyn.* 7:63–73, 1989, both of which are herein incorporated by reference).

EXAMPLE 8

DETERMINING THE SEQUENCE OF A TEMPLATE USING SEQUENCE PRIMERS WITH FOUR SPECIFIC BASES

This reaction was performed using same steps as outlined in Example 8. However, sequencing reagents with a sequence specific hybridizing region of 4 bases were employed. This results of this experiment, which are depicted in Table 3, show that a sequence specific region of 4 bases is also effective at priming the polymerase extension reaction.

By aligning the sequence reagents Table 1, with the results of Table 3, one of skill in the art could determine that the sequence of the template molecule is 5'-ACT-3'.

TABLE 3

| labeled ddNTP | SEQ ID NO. 2 | SEQ ID NO. 12 | SEQ ID NO. 9 | SEQ ID NO. 13 | SEQ ID NO. 14 | SEQ ID NO. 15 |
| --- | --- | --- | --- | --- | --- | --- |
| A | 1.537 | 1.366 | 0.161 | 0.142 | 0.142 | 0.146 |
| A | 1.686 | 1.475 | 0.165 | 0.143 | 0.143 | 0.143 |
| C | 0.146 | 0.151 | 2.213 | 1.400 | 0.121 | 0.124 |
| C | 0.150 | 0.156 | 2.146 | 1.423 | 0.123 | 0.130 |
| G | 0.140 | 0.211 | 0.205 | 0.202 | 0.120 | 0.134 |
| G | 0.145 | 0.211 | 0.203 | 0.195 | 0.119 | 0.135 |
| T | 0.118 | 0.141 | 0.148 | 0.140 | 1.168 | 1.027 |
| T | 0.117 | 0.139 | 0.148 | 0.142 | 1.234 | 0.943 |

EXAMPLE 9

DETERMINING THE SEQUENCE OF A TEMPLATE USING A CAPTURE MOIETY THAT IS CO-ATTACHED WITH A SEQUENCING REAGENT

This experiment tests whether the capture moiety and the sequence specific hybridizing region co-attached to the well of a 96-well plate as separate moieties can be used to sequence a template. The hybridization and extension reactions are exactly as described in Example 7. The expected signal is T.

Figure 2A:
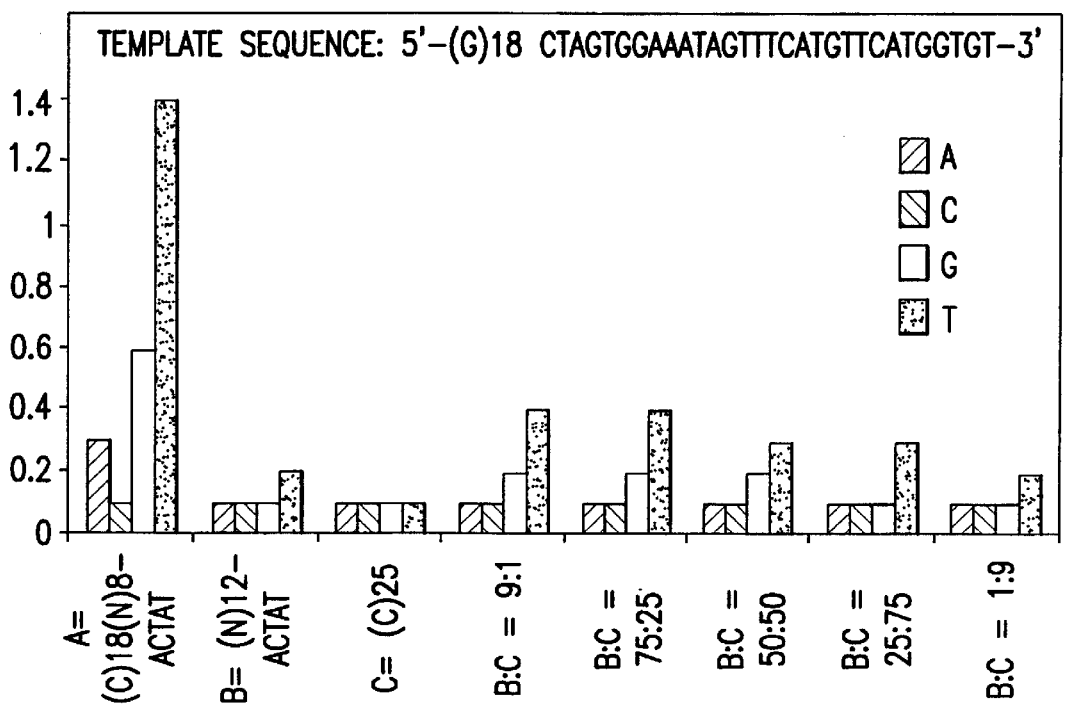
FIGS. 2A and 2B provide the results of an extension reaction wherein the capture moiety and the sequence specific hybridizing region are on separate molecules.

As shown in FIG. 2A, the capture moiety and sequence specific hybridizing region, as a separate moieties, are capable of capturing the template sequence and priming the extension reaction. However, the efficiency of the extension reaction is not as high as seen when the capture moiety and sequence specific hybridizing region are in the same sequencing reagent.

Figure 2B:
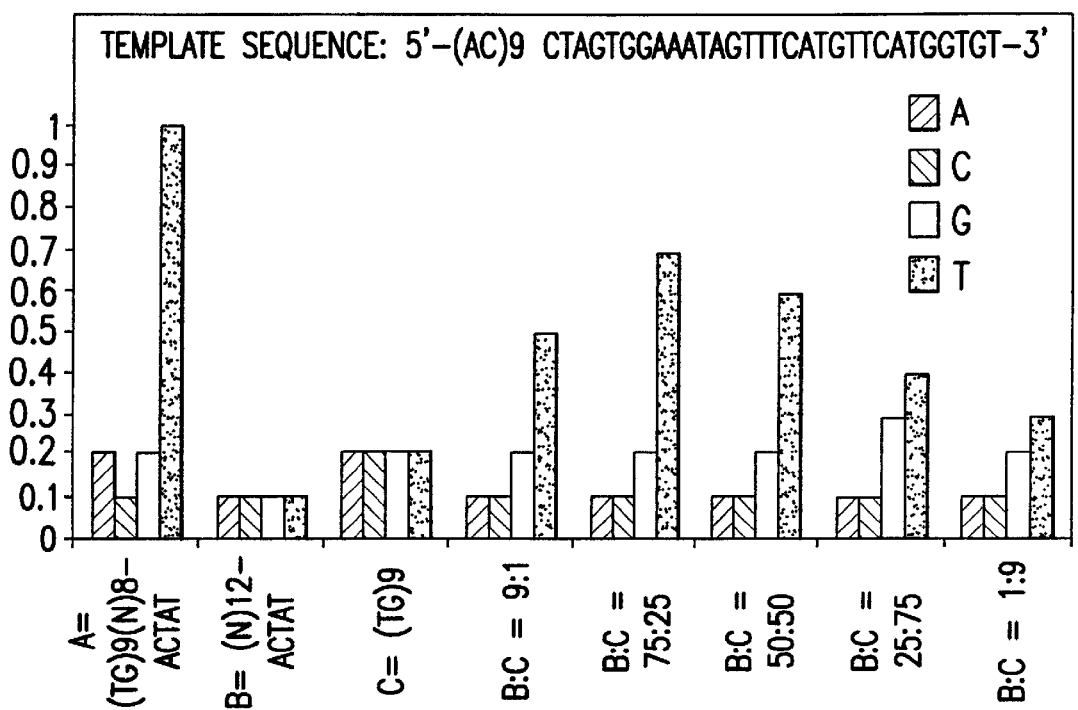

As shown in FIG. 2B, the efficiency of the extension reaction where the capture moiety and sequence specific hybridizing region exist as a separate moieties, approaches that seen where the capture moiety and sequence specific hybridizing region are in the same sequencing reagent when a different template sequence is used. From these experiments, it is apparent that the efficiency of the extension reaction is dependent upon the sequence of the template moiety and the capture moiety.

EXAMPLE 10

DETERMINING THE SEQUENCE OF A TEMPLATE USING A PRIMER WITH A CAPTURE SEQUENCE AND A SEVEN BASE HYBRIDIZATION REGION

In this experiment, a 7 mer (SEQ ID NO. 31) was used to sequence two template sequences (SEQ ID NO. 29 and SEQ ID NO. 31). The hybridization and extension reactions are exactly as described in Example 8. The expected signal is A. This experiment tests whether a 7 mer can act as both a capture sequence and a sequence specific hybridizing region. The results of this experiment are shown in Table 4.

TABLE 4

| labeled ddNTP | SEQ ID NO. 29 | SEQ ID NO. 30 |
| --- | --- | --- |
| A | 1.206 | 0.688 |
| A | 1.088 | 0.989 |
| C | 0.12 | 0.109 |
| C | 0.124 | 0.134 |
| G | 0.144 | 0.186 |
| G | 0.147 | 0.193 |
| T | 0.117 | 0.126 |
| T | 0.114 | 0.132 |

As can be seen in Table 4, a 7 mer can act as both a capture moiety and a sequence specific hybridizing region. However, the sequencing reagent is best able to prime the extension reaction when the capture moiety and the sequence specific hybridizing region are not the same.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

---

We claim:

1. A sequencing reagent comprising:
   i) a capture moiety which can form a stable complex with a region of a template nucleic acid molecule;
   ii) a spacer region; and
   iii) a sequence specific hybridizing region, 4–8 bases in length, which is bound to the spacer region, and which can hybridize to a complementary sequence on the template nucleic acid molecule.

2. The sequencing reagent of claim 1, wherein said reagent further comprises an attachment moiety which permits for attachment of the primer to a solid surface.

3. The sequencing reagent of claim 2, wherein said attachment moiety is at or near the 5' terminus of the primer.

4. The sequencing reagent of claim 2, wherein said attachment moiety is selected from the group consisting of amino, thiol, disulfide, avidin, strepavidin, iminobiotin, biotin, antibody and hapten.

5. The sequencing reagent of claim 1, wherein said capture moiety comprises either a nucleic acid sequence selected from the group of nucleotide analogs consisting of DNA, RNA and protein nucleic acid (PNA) or the group of non-nucleotide capture moieties consisting of biotin, iminobiotin, avidin, strepavidin, antibody, hapten, receptor, ligand and charged base and their analogs.

6. The sequencing reagent of claim 5, wherein said capture moiety nucleic acid sequence comprises a sequence of 8–24 C bases.

7. The sequencing reagent of claim 1, wherein said capture moiety comprises a specific sequence complementary to a PCR primer, or portion thereof.

8. The sequencing reagent of claim 1, wherein said capture moiety is selected from the group consisting of biotin, iminobiotin, avidin, strepavidin, antibody, hapten, receptor, ligand and charged base.

9. The sequencing reagent of claim 1, wherein said spacer region is at least 10 nm in length.

10. The sequencing reagent of claim 1, wherein said spacer region comprises a region of random, pseudo-random or non-random bases or analogs thereof.

11. The sequencing reagent of claim 1, wherein said spacer region comprises polyethylene glycol.

12. The sequencing reagent of claim 1, wherein said spacer region is designed to minimize template independent noise.

13. The sequencing reagent of claim 1, wherein said sequence specific region comprises 4–6 bases which can hybridize to a complementary sequence on the template nucleic acid molecule.

14. The sequencing reagent of claim 1, wherein said sequence specific region comprises 6 bases which can hybridize to a complementary sequence on the template nucleic acid molecule.

15. An array of sequencing array reagents, comprising an orderly arrangement of a plurality of sequencing array reagents immobilized to a solid surface wherein each of said sequencing array reagents comprises:

i) a capture moiety which can form a stable complex with a region of a template nucleic acid molecule;

ii) a spacer region; and iii) a sequence specific hybridizing region, wherein said sequence specific region comprises 4–8 bases which can hybridize to a complementary sequence on the template nucleic acid molecule.

16. The array according to claim 15, wherein said array comprises a set, subset or combination of $4^4$–$4^8$ different sequence reagents.

17. The array according to claim 15, wherein said array comprises $4^4$ different sequence reagents.

18. The array according to claim 15, wherein said array comprises $4^5$ different sequence reagents.

19. The array according to claim 15, wherein said array comprises $4^6$ different sequence reagents.

20. The array according to claim 15, wherein said array comprises $4^7$ different sequence reagents.

21. The array according to claim 15, wherein said array comprises $4^8$ different sequence reagents.

22. The array according to claim 15, wherein said array comprises an array of nested sequencing reagents.

* * * * *

UNITED STATES PATENT AND TRADEMARK OFFICE
CERTIFICATE OF CORRECTION

PATENT NO. : 6,322,968 B1
DATED : November 27, 2001
INVENTOR(S) : S. R. Head et al.

It is certified that error appears in the above-identified patent and that said Letters Patent is hereby corrected as shown below:

<u>Title page,</u>
Item [56], References Cited, U.S. PATENT DOCUMENTS, please add the following references:

| PATENT NO. | TITLE | ISSUE DATE |
|---|---|---|
| 5,744,305 Fodor, S.P.A et al. | Arrays of Materials Attached to a Substrate | April 28, 1998 |
| 5,700,637 Southern, E. | Apparatus and Method for Analyzing Polynucleotide Sequences and Method of Generating Oligonucleotide Arrays | December 23, 1997 |
| 5,795,714 Cantor et al. | Method for Replicating an Array of Nucleic Acid Probes | August 18, 1998 |
| 5,002,867 Macevicz, S.C. | Nucleic Acid Sequence Determination by Multiple Mixed Oligonucleotide Probes | March 26, 1991 |
| 4,851,331 Vary, C.P.H. et al. | Method and Kit for Polynucleotide Assay Including Primer-Dependent DNA Polymerase | July 25, 1989 |
| 5,053,100 Hayes, D.J. et al. | Method of Making Apparatus for Dispensing Small Amounts of Fluids | October 1, 1991 |
| 4,521,509 Benkovic, S. J. et al. | Method for Degrading DNA | June 4, 1985 |
| 4,981,783 Augenlicht, L. | Method for Detecting Pathological Conditions | January 1, 1991 |
| 5,503,980 Cantor, C.R. | Positional Sequencing by Hybridization | April 2, 1996 |
| 5,518,900 Nikiforov, T.T. et al. | Method for Generating Single-Stranded DNA Molecules | May 21, 1996 |

UNITED STATES PATENT AND TRADEMARK OFFICE
CERTIFICATE OF CORRECTION

PATENT NO.     : 6,322,968 B1
DATED          : November 27, 2001
INVENTOR(S)    : S. R. Head et al.

It is certified that error appears in the above-identified patent and that said Letters Patent is hereby corrected as shown below:

References Cited, FOREIGN PATENT DOCUMENTS, please add the following references:

| DOCUMENT NO. | TITLE | PUBLICATION DATE |
|---|---|---|
| WO 96/17957 Drmanac, R.T. | Methods and Apparatus for DNA Sequencing and DNA Identification | 13 June 1996 |
| WO 95/03401 Gruber, L.S. et al. | Method for Screening Unknown Organisms | 2 February 1995 |

References Cited, OTHER PUBLICATIONS, please add the following references:

Antrazhev et al., 3' Substituted Nucleoside Phosphothioates Terminate DNA Synthesis Catalyzed by Various DNA Polymerases, Bio-org Khim 13:1045-1052 (1987).

Beattie, W.G. et al., Hybridization of DNA Targets to Glass-Tethered Oligonucleotide Probes, Molecular Biotechnology, 4: 213-225 (1995).

Beattie, K.L. et al., Solid-phase gene assembly, Nature, 352: 348-549 (1991).

Botstein, D. et al., Construction of a Genetic Linkage Map in Man Using Restriction Fragment Length Polymorphisms, American Journal of Human Genetics, 32: 314-331 (1980).

Carlsson, J. et al., Solid-Phase Disulfide Oxides: A New Approach to Reversible Immobilization and Covalent Chromatography of Thiol Compounds, Biotechnology and Applied Biochemistry, 14: 114-120 (1991).

Chidgeavadze, Z.G. et al., 3'-Fluoro-2',3'-dideoxyribonucleoside 5'-triphosphates: terminators of DNA synthesis, FEBS Letters, 183: 275-278 (1985).

Chidgeavadze, Z.G. et al., Nucleoside 5'-triphosphates with modified sugars as substrates for DNA polymerases, Biochem Biophys Acta, 868:145-152 (1986).

Chidgeavadze, Z.G. et al., Conformationally Restricted 5'-Triphosphates as Termination Substrates for DNA Polymerases, Mol Biol (Mosk.), 23:1732-1742 (1989).

Chu, C.F.B. et al., Ligation of oligonucleotides to nucleic acids or proteins via disulfide bonds, Nucleic Acids Research, 16: 3671-3691 (1988).

UNITED STATES PATENT AND TRADEMARK OFFICE
CERTIFICATE OF CORRECTION

PATENT NO. : 6,322,968 B1
DATED : November 27, 2001
INVENTOR(S) : S. R. Head et al.

It is certified that error appears in the above-identified patent and that said Letters Patent is hereby corrected as shown below:

Conner, B.J. et al., Detection of sickle cell ß$^S$ -globin allele by hybridization with synthetic oligonucleotides, Proc. Natl. Acad. Sci. USA, 80: 278-282 (1983)

Eckstein, F. et al., Synthesis and Properties of Diastereoisomers of Adenosine 5'-(0-1- Thiotriphosphate) and Adenosine 5'-(0-2-Thiotriphosphate), Biochemistry, 15:1685-1691(1976).

Engelke, D.R. et al., Direct sequencing of enzymatically amplified human genomic DNA, Proc. Natl. Acad. Sci. USA, 85: 544-548 (1988).

Fahy, E. et al., Design and synthesis of polyacrylamide-based oligonucleotide supports for use in nucleic acid diagnostics, Nucleic Acids Research, 21: 1819-1826 (1993).

Guo, Zhen et al., Direct fluorescence analysis of genetic polymorphisms by hybridization with oligonucleotide arrays on glass supports, Nucleic Acids Research, 22: 5456-5465 (1994).

Gyllensten, U.B. et al., Generation of single-stranded DNA by the polymerase chain reaction and its application to direct sequencing of the HLA-DQA locus, Proc. Natl. Acad. Sci. USA, 85: 7652-7656 (1988).

Haff, L.A. et al., Single-Nucleotide Polymorphism Identification Assays Using a Thermostable DNA Polymerase and Delayed Extraction MALDI-TOF Mass Spectrometry, Genome Research, 7: 378-388 (1997).

Herrlein, M.K. et al., 3'-Amino-Modified Nucleotides Useful as Potent Chain Terminators for Current DNA Sequencing Methods, Helvetica Chimica Acta, 77: 586-596 (1994).

Higuchi, R.G. et al., Production of single-stranded DNA templates by exonuclease digestion following the polymerase chain reaction, Nucleic Acids Research, *17*:5865 (1989).

Holmstrom, K. et al., A Highly Sensitive and Fast Nonradioactive Method for Detection of Polymerase Chain Reaction Products, Analytical Biochemistry, 209: 278-283 (1993).

Jalanko, A. et al., Screening for Defined Cystic Fibrosis Mutations by Solid-phase Minisequencing, Clin. Chem., 38: 39-43 (1992).

UNITED STATES PATENT AND TRADEMARK OFFICE
CERTIFICATE OF CORRECTION

PATENT NO.   : 6,322,968 B1
DATED        : November 27, 2001
INVENTOR(S)  : S. R. Head et al.

It is certified that error appears in the above-identified patent and that said Letters Patent is hereby corrected as shown below:

Kawai, S. et al., A Simple Method of Detecting Amplified DNA with Immobilized Probes on Microtiter Wells, Analytical Biochemistry, 209: 63-69 (1993).

Kornberg, A. et al., DNA Replication: Second Edition, Freeman W.H. &Co. : San Francisco pp. 408, 446-449 (1992).

Lamture, J.B. et al., Direct detection of nucleic acid hybridization on the surface of a charge coupled device, Nucleic Acids Research, 22: 2121-2125 (1994).

Landegren, U. et al., A Ligase-Mediated Gene Detection Technique, Science, 241: 1077-1080 (1998).

Maskos, U. et al., Oligonucleotide hybridisations on glass supports: a novel linker for oligonucleotide synthesis and hybridisation properties of oligonucleotides synthesised in situ, Nucleic Acids Research, 20: 1679-1684(1992).

Matteucci, M.D. et al., Synthesis of Deoxyoligonucleotides on a Polymer Support, J. Am. Chem. Soc., 103: 3185-3191(1981).

Maxam, A.M. et al., A New Method for Sequencing DNA, Proc. Natl. Acad. Sci. USA, 74: 560-564 (1977).

Messing, J., New M13 Vectors for Cloning, Methods in Enzymology, 10: 20-78 (1983).

Miholovic, M. et al., An Efficient Method for Sequencing PCR Amplified DNA, Biotechniques, 7: 14-16 (1989).

Mitsuya, H. et al., Inhibition of the in vitro infectivity and cytopathic effect of human T-lymphotrophic virus type III/lymphadenopathy-associated virus (HTLV-III/ LAV) by 2',3'-dideoxynucleosides, Proc. Natl. Acad. Sci. USA, 83: 1911-1915 (1986).

Newton, C.R. et al., The production of PCR products with 5' single-stranded tails using primers that incorporate novel phosphoramidite intermediates, Nucleic Acids Research, 21: 155-1162 (1993).

Nickerson, D.A. et al., Automated DNA diagnostics using an ELISA-based oligonucleotide ligation assay, Proc. Natl. Acad. Sci. USA, 87: 8923-8927 (1990).

UNITED STATES PATENT AND TRADEMARK OFFICE
CERTIFICATE OF CORRECTION

PATENT NO. : 6,322,968 B1
DATED : November 27, 2001
INVENTOR(S) : S. R. Head et al.

It is certified that error appears in the above-identified patent and that said Letters Patent is hereby corrected as shown below:

Ott, J. et al., Protection of Oligonucleotide Primers against Degradation by DNA Polymerase 1, Biochemistry, 26: 8237-8241 (1987)

Pease, A.C. et al., Light-generated oligonucleotide arrays for rapid DNA sequence analysis, Proc. Natl. Acad. Sci. USA, 91: 5022-5026 (1994).

Prober, J. M. et al., A System for Rapid DNA Sequencing with Fluorescent Chain-Terminating Dideoxynucleotides, Science, 238: 336-340 (1987).

Rasmussen, S.R. et al., Covalent Immobilization of DNA onto Polystyrene Microwells: The Molecules Are Only Bound at 5' End, Analytical Biochemistry, 198: 138-142 (1991).

Running, J.A. et al., A Procedure for Productive Coupling of Synthetic Oligonucleotides to the Polystyrene Microtiter Wells for Hybridization Capture, BioTechniques, 8:276-277 (1990).

Sanger, F. et al., A Rapid Method for Determining the Sequences in DNA by Primed Synthesis with DNA Polymerase, J. Mol. Biol., 94: 441-448 (1975).

Sayers, J.R. et al., 5'-3' Exonucleases in phosphorothioate-based oligonucleotide-directed mutagenesis, Nucleic Acids Research, 16: 791-802 (1988).

Sliwkowski, M.X. et al., Resolution of sulphydryl oxidase fromY -glutamyltransferase in bovine milk by covalent chromatography on cysteinylsuccinamidopropyl-glass, Biochem J., 209: 731-739 (1983).

Southern, E.M. et al. Arrays of complementary oligonucleotides for analysing the hybridisation behaviour of nucleic acids, Nucleic Acids Research, 22: 1368-1373 (1994).

Spiegelman, S., Hybrid Nucleic Acids, Scientific American, 210: 48-56 (1964).

White, R. et al., Chromosome mapping with DNA markers, Scientific American, 258: 40-48 (1988).

Wong, C. et al., Characterization of β-thalassaemia mutations using direct genomic sequencing of amplified single copied DNA, Nature, 330: 384-386 (1987).

Yuzhakov, A.A. et al., 3'-Mercapto-2', 3-dideoxynucleotides are high effective terminators of DNA synthesis catalyzed by HIV reverse transcriptase, FEBS Letters, 306: 185-188 (1992).

UNITED STATES PATENT AND TRADEMARK OFFICE
CERTIFICATE OF CORRECTION

PATENT NO.    : 6,322,968 B1
DATED         : November 27, 2001
INVENTOR(S)   : S. R. Head et al.

It is certified that error appears in the above-identified patent and that said Letters Patent is hereby corrected as shown below:

<u>Column 3,</u>
Line 8, In Table 1, SEQ ID NO. 13 (corresponding to the Expected Signal) please delete "T" and insert -- C --.

<u>Column 8,</u>
Lines 2-3, Table 2, please delete the heading "SEQ ID NO. 5" and insert
-- SEQ ID NO. 4 --.

<u>Column 4,</u>
Lines 2-3, Table 3, please delete the heading "SEQ ID NO. 9" and insert
-- SEQ ID NO. 3 --.

Signed and Sealed this

Twenty-fourth Day of September, 2002

Attest:

JAMES E. ROGAN
*Attesting Officer*     *Director of the United States Patent and Trademark Office*